United States Patent
Shinada et al.

(10) Patent No.: US 6,797,954 B2
(45) Date of Patent: Sep. 28, 2004

(54) PATTERNED WAFER INSPECTION METHOD AND APPARATUS THEREFOR

(75) Inventors: Hiroyuki Shinada, Chofu (JP); Yusuke Yajima, Kodaira (JP); Hisaya Murakoshi, Suginami-ku (JP); Masaki Hasegawa, Hachioji (JP); Mari Nozoe, Oume (JP); Atsuko Takafuji, Nerima-ku (JP); Katsuya Sugiyama, Kashiwa (JP); Katsuhiro Kuroda, Hachioji (JP); Kaoru Umemura, Musashino (JP); Yasutsugu Usami, Toshima-ku (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/400,588

(22) Filed: Mar. 28, 2003

(65) Prior Publication Data

US 2003/0164460 A1 Sep. 4, 2003

Related U.S. Application Data

(63) Continuation of application No. 09/164,366, filed on Oct. 1, 1998, now abandoned.

(30) Foreign Application Priority Data

Oct. 2, 1997 (JP) .............................................. 9-269500

(51) Int. Cl.[7] .............................................. H01J 37/244
(52) U.S. Cl. .................... 250/310; 250/311; 250/442.11
(58) Field of Search ................................ 250/310, 311, 250/442.11, 306, 305

(56) References Cited

U.S. PATENT DOCUMENTS

| 4,978,855 | A | | 12/1990 | Liebl et al. |
|---|---|---|---|---|
| 5,389,787 | A | * | 2/1995 | Todokoro et al. ........... 250/310 |
| 5,578,821 | A | | 11/1996 | Meisberger et al. |
| 5,767,516 | A | | 6/1998 | Kawanami et al. |
| 6,172,363 | B1 | * | 1/2001 | Shinada et al. ............. 250/310 |
| 6,184,526 | B1 | | 2/2001 | Kohama et al. |

FOREIGN PATENT DOCUMENTS

| JP | 59-192943 | 11/1984 |
|---|---|---|
| JP | 5-258703 | 10/1993 |

OTHER PUBLICATIONS

Journal of Vacuum Science and Technology B, vol. 9, No. 6, Nov./Dec. 1991, "An electron–beam inspection system for x–ray mask production", P. Sandford.
Journal of Vacuum Science and Technology B, vol. 10, No. 6, Nov./Dec. 1992, Low–voltage electron–optical system for the high–speed inspection of integrated circuits, W.D. Meisburger et al, pp. 2804–2808.
SPIE, vol. 2439, pp. 174–183.

* cited by examiner

*Primary Examiner*—Nikita Wells
*Assistant Examiner*—Anthony Quash
(74) *Attorney, Agent, or Firm*—Mattingly, Stanger & Malur, P.C.

(57) ABSTRACT

An electron beam (area beam) having a fixed area is irradiated onto the surface of a semiconductor sample, and reflected electrons from the sample surface are imaged by the imaging lens, and images of a plurality of regions of the surface of the semiconductor sample are obtained and stored in the image storage unit, and the stored images of the plurality of regions are compared with each other, and the existence of a defect in the regions and the defect position are measured. By doing this, in an apparatus for testing a pattern defect of the same design, foreign substances, and residuals on a wafer in the manufacturing process of a semiconductor apparatus by an electron beam, speeding-up of the test can be realized.

7 Claims, 7 Drawing Sheets

PATTERNED WAFER INSPECTION METHOD AND APPARATUS THEREFOR

This is a continuation application of U.S. Ser. No. 09/164,366, filed Oct. 1, 1998, now abandoned

BACKGROUND OF THE INVENTION

1. Field of the Invention

The present invention relates to a method for testing the surface status of a sample (a semiconductor device, etc.) and apparatus therefor and particularly to an inspection method and apparatus therefor for imaging and inspecting fine pattern defects on the surface of a semiconductor device in high sensitivity and high resolution at high speed using an electron beam.

2. Description of the Prior Art

As an inspecting method for detecting defects of a circuit pattern formed on a wafer by comparison test in the manufacturing process of a semiconductor device, there is a method for obtaining images of two or more same kind of LSI patterns on one wafer using light, comparing these plurality of images, and testing existence of pattern defects and it is already put into practical use. The outline of this inspecting method is described in "Monthly Semiconductor World", October issue, 1995, pp. 114 to 117. When pattern defects in the manufacturing process of a semiconductor device are tested by such an optical inspecting method, residuals of a silicon oxide film through which light transmits and a photosensitive resist material cannot be detected. Residual etching below the resolution of the optical system and a nonopening defect of a fine conducting hole can be neither detected.

To solve such a problem in the optical inspecting method, a pattern comparison inspecting method using an electron beam is described in Japanese Patent Application Laid-Open 59-192943, J. Vac. Sci. Tech. B, Vol. 9, No. 6, pp. 3005–3009 (1991), J. Vac. Sci. Tech. B, Vol. 10, No. 6, pp. 2804–2808 (1992), SPIE, Vol. 2439, pp. 174 0 183, and Japanese Patent Application Laid-Open 05-158703. In this case, to obtain a practical inspecting speed, it is necessary to obtain pattern images at a very high speed. To reserve the S/N ratio of images obtained at high speed, a beam current more than 100 times (more than 10 nA) of that of a normal scanning electron microscope is used.

In the aforementioned prior testing art using an electron beam, to form images maintaining the S/N ratio which can be tested, an electron beam having a large current is used. However, since the electron beam is limited to a spot shape and this spot beam is two-dimensionally scanned on the surface of a sample, there is a limit to the high speed (shortening of the inspecting time). There is also a limit to the large current of an electron beam to be used due to the brightness of the electron source used and space charge effect. For example, to obtain a resolution of about 0.1 $\mu$m, the electron beam current to be used is theoretically limited to about several hundreds nA and only about 100 nA can be actually used. The S/N ratio of an image is decided by the number of electrons to be used so as to form the image, that is, the product of beam current and time required to obtain the image. In consideration of necessity of reservation of the S/N ratio on the image processing ready level, to obtain a resolution of 0.1 $\mu$m at a beam current of 100 nA, about 100 seconds or more are required to test an area of 1 cm$^2$ of the surface of a sample. On the other hand, in the aforementioned conventional optical inspection apparatus, the test required time for an inspection area of 1 cm$^2$ is very short such as about 5 seconds.

SUMMARY OF THE INVENTION

Therefore, an object of the present invention is to shorten the test required time of the pattern comparison inspecting method using an electron beam such as equal to or less than that of the conventional optical inspecting method.

To accomplish this object, the present invention is a pattern defect inspecting method and apparatus therefor for spreading and irradiating an electron beam from the electron source to a fixed area region on the surface of a sample at the same time, imaging backscattering electrons obtained from the area region or secondary electrons and forming an enlarged image of the area region, moving the sample so as to irradiate the electron beam at the desired location of the surface of the sample, converting the enlarged image of the area region formed by the aforementioned image forming means to an image signal, and comparing the image signal of one area region on the surface of the sample obtained by the aforementioned image signal obtaining means with an image signal of another area region and detecting a pattern defect in the one area region.

Furthermore, the pattern defect inspecting method and apparatus therefor of the present invention is characterized in that the method and apparatus include at least first electron beam irradiation for spreading and irradiating an electron beam from the electron source to a first area region on the surface of a sample at the same time, first electron image forming for imaging backscattering electrons emitted from the first area region or secondary electrons and forming a first electron image of the first area region, first image signal obtaining for obtaining an image signal of the first electron image of the first area region, irradiation position movement for moving the electron beam irradiation position from the first area region on the surface of the sample to a second area region, second electron beam irradiation for spreading and irradiating the electron beam from the electron source to the second area region on the surface of the sample at the same time, second electron image forming for imaging backscattering electrons emitted from the second area region or secondary electrons and forming a second electron image of the second area region, second image signal obtaining for obtaining an image signal of the second electron image of the second area region, and defect detection for comparing the image signal of the first electron image of the first area region obtained at the aforementioned first image signal obtaining stage with the image signal of the second electron image of the second area region obtained at the aforementioned second image signal obtaining stage and detecting a pattern defect in the first area region or the second area region.

More concretely, the above object of the present invention, that is, speeding-up of the pattern comparison inspecting method using an electron beam is realized by sequentially irradiating an electron beam to a plurality of irradiation regions (area regions) of the surface of a sample as an area beam having a two-dimensional spread instead of a spot beam, sequentially forming enlarged images of the plurality of irradiation regions by imaging backscattering electrons from the plurality of irradiation regions (area regions) or secondary electrons, converting the enlarged images of the plurality of irradiation regions to electrical image signals, and detecting a pattern defect in each of the aforementioned irradiation regions by comparing the image signals in the plurality of irradiation regions with each other.

Namely, in the patterned wafer inspection method of the present invention, an electron beam from the electron source is sequentially irradiated to a plurality of irradiation regions (area regions) of the surface of a semiconductor sample as a so-called area beam, and enlarged images in the plurality of irradiation regions are sequentially formed by electron-optically imaging backscattering electrons from the plurality of irradiation regions or secondary electrons, and the enlarged images in the plurality of irradiation regions are sequentially converted to electrical image signals and stored, and a pattern defect in each of the aforementioned irradiation regions is detected by comparing the stored image signals in the plurality of irradiation regions with each other. According to this method, the conventional two-dimensional scanning by a spot beam in each irradiation region (area region) is not necessary, so that the inspection time can be greatly shortened and the defect test can be speeded up.

The patterned wafer inspection apparatus of the present invention can comprise an electron optical system for irradiating an electron beam from the electron source to the surface of a semiconductor sample as an area beam and forming an enlarged image in the irradiated region by imaging backscattering electrons from the irradiation region (area region) or secondary electrons, a sample moving stage for loading the semiconductor sample and moving the semiconductor sample so that the electron beam is irradiated at the desired position on the surface of the semiconductor sample, an image signal detection means for converting and detecting the enlarged image to an electrical image signal, and an image signal processing means for detecting a pattern defect in each irradiation region by comparing the image signal in a plurality of irradiation regions on the surface of the semiconductor sample detected by the image signal detection means.

It is valid to decelerate the electron beam irradiated onto the sample surface by applying a negative potential to the sample and let the decelerated electron beam enter the sample surface or reflect from the neighborhood of the pole without entering the sample surface.

When the sample moving stage is set so as to continuously move the sample at almost uniform velocity, more speeding-up of the defect inspection can be realized. In this case, needless to say, by providing a stage position monitoring means for monitoring the position of the sample moving stage, it is necessary to control so that the electron beam irradiation region on the sample surface is kept at the same position on the sample surface for a predetermined time.

Furthermore, the image signal detection means converts the enlarged electron image of the irradiation region imaged and formed by the electron optical system to an optical image by projecting it onto the fluorescence plate and images the optical image on the optical image detection device via the optical lens or optical fiber. Or, the enlarged electron image formed by the electron optical system may be directly formed on the image detection device having electron sensitivity. As an image detection device, a charge coupled device (CCD sensor) or a device for integrating and outputting an optical signal inputted with the time delayed can be used. To read a detection signal from the image detection device, a system for reading by many channels in parallel is used.

On the other hand, a method for setting so that the size of enlarged images on the surface of a semiconductor sample which can be obtained at the same time by irradiating an electron beam at the same time becomes almost equal to the size of the light receiving surface of the image detection device is simpler. On the other hand, by setting the size of the electron beam irradiation region so that the size of enlarged images on the surface of a semiconductor sample is made smaller than the size of the light receiving surface of the image detection device, scanning the electron beam on the surface of the semiconductor sample, then projecting the enlarged images overall the light receiving surface of the image detection device for a given period of time, and superimposing a signal for correcting the variation factors of irradiation position and irradiation range on the scanning signal of the electron beam, a method realizing higher precision may be available.

To decelerate an electron beam to be irradiated onto a semiconductor sample, make the energy value of the electron beam when it is irradiated onto the sample sufficiently smaller than the energy value before deceleration, and keep the energy dispersion of backscattering electrons generated from the sample surface by irradiation of the decelerated electron beam within a range that it will not affect the resolution of the imaging system, a negative potential is applied to the semiconductor sample. Or, by providing a filter for discriminating backscattering electrons generated by irradiation of the electron beam or secondary electrons in energy and imaging only backscattering electrons or secondary electrons with a specific energy width, the problem of high speed test can be solved and the resolution can be improved at the same time.

The foregoing and other objects, advantages, manner of operation and novel features of the present invention will be understood from the following detailed description when read in connection with the accompanying drawings.

DETAILED DESCRIPTION OF THE PREFERRED EMBODIMENTS

The present invention will be explained in detail hereunder with reference to the embodiments.

Embodiment 1

Figure 1:
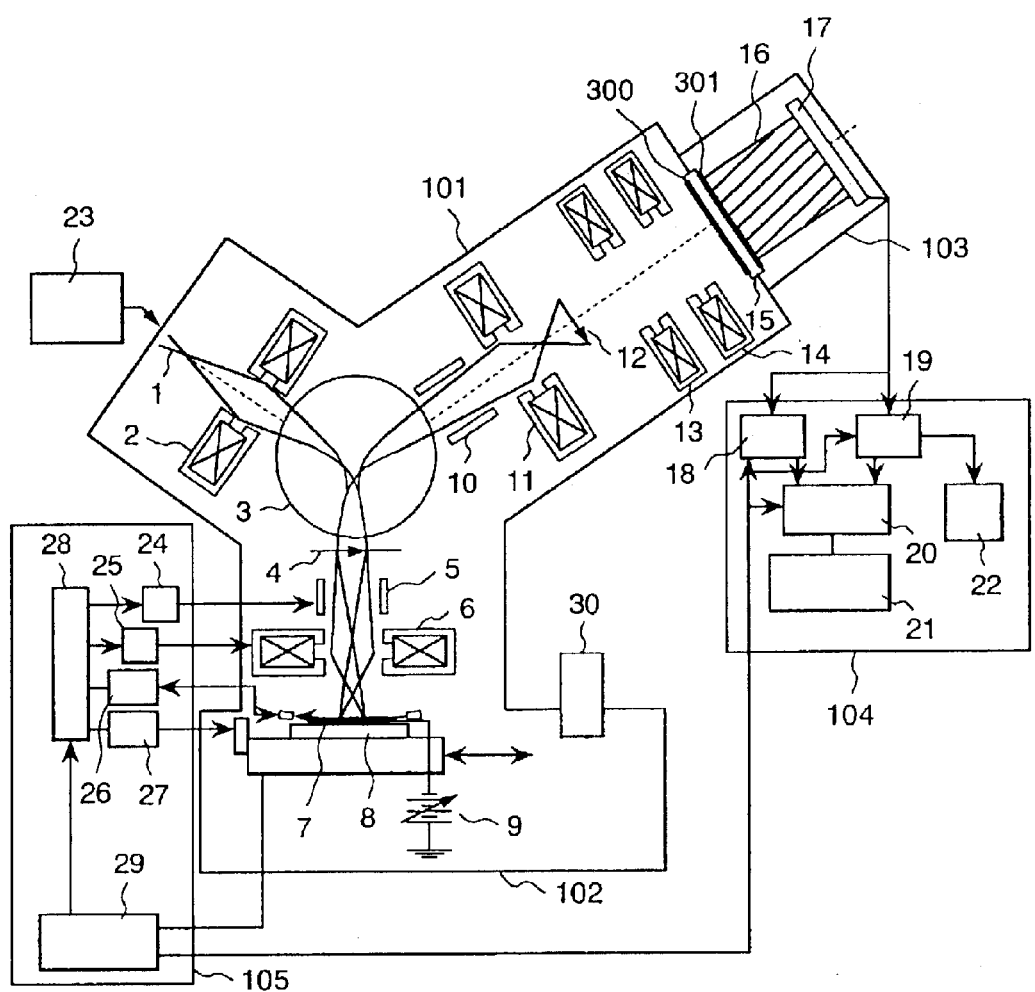
FIG. 1 is a schematic view of the inspection apparatus of the first embodiment of the present invention.

FIG. 1 shows a schematic view of the inspection apparatus which is an embodiment of the present invention. The inspection apparatus of the present invention broadly comprises an electron optical system 101, a sample chamber 102, an image detector 103, an image processor 104, and a controller 105.

Firstly, the electron optical system 101 will be explained. An acceleration electron beam emitted from an electron source 1 which is given a negative high potential from an acceleration power source 23 is focused by a condenser lens 2 and irradiated onto an aperture 4 having a rectangular opening. The electron beam is deflected by an electromagnetic deflector 3 before it is irradiated onto the aperture 4. The electromagnetic deflector 3 is used to separate the path of an incoming electron beam from the electron source 1 from the path of a reflected electron (backscattering electron or secondary electron) beam from a sample. An incoming electron beam passing through the rectangular limiting opening of the aperture 4 is imaged by an object lens 6 and forms an image of the rectangular limiting opening on the surface of a semiconductor sample 7. The size of the rectangular limiting opening on the aperture 4 is, for example, a square of 400 μm and reduced to ¼ by the object lens 6 and a limiting opening image (irradiation region) of a square of 100 μm is obtained on the surface of the sample 7. The limiting opening image (irradiation region) can be moved (or scanned) to an optional position on the surface of the sample 7 by a deflector in an illumination system 5. In the electron source 1, a LaB6 thermionic source having a flat tip in which the flat portion is 10 μm or more in diameter is used. By using it, an electron beam can be uniformly irradiated in a wide area (irradiation region) on the surface of the sample 7.

To the sample 7 and a sample moving stage 8, a negative potential lower (a small absolute value) or slightly higher (a large absolute value) than that of the electron source 1 is applied by a power source 9. A negative potential slightly lower than the potential of the electron source 1 is applied only when backscattering electrons from the sample 7 are used for inspection. In this case, an incoming electron beam is decelerated before the sample 7 by the aforementioned negative potential, travels toward the surface of the sample 7, and is scattered backward by atoms of the surface of the sample 7. The backscattered electrons are led to an imaging lens 11 via the electromagnetic deflector 3 and a deflector in an imaging system 10 and imaged as a scattered electron image 12. Furthermore, when the scattered electron image 12 is enlarged and projected on a fluorescence plate 15 by magnifying lenses 13 and 14, a fluorescence image (microscopic image) reflecting the surface pattern of the sample 7 can be obtained.

In the sample chamber 102, the sample 7 is loaded on the sample moving stage 8 movable in the two-dimensional directions (X, Y, O) and the aforementioned negative potential is applied to the sample 7 by the power source 9. The sample moving stage 8 is equipped with a stage position measuring apparatus 27 and accurately measures the stage position in real time. The reason is that images are obtained by continuously moving the stage 8. As the stage position measuring apparatus 27, for example, a laser interference meter is used. To accurately measure the height of the surface of a semiconductor sample (wafer), an optical sample height measuring apparatus 16 is also mounted. As the measuring apparatus, for example, a system for entering light obliquely into the inspection region on the wafer surface and measuring the height of the wafer surface from a change in the position of the reflected light can be used. In addition, in the sample chamber 102, an optical microscope 30 used to position the inspection region is also mounted.

Next, the image detector 103 will be explained. For image detection, the fluorescence plate 15 for converting an enlarged image of the scattered electron image 12 to an optical image and an optical image detection device (for example, CCD device) 17 are optically connected by an optical fiber bundle 16. By doing this, the optical image on the fluorescent plate 15 is imaged on the light receiving surface of the optical image detection device 17. The optical fiber bundle 16 comprises thin optical fibers whose number is equal to the number of pixels. It is possible to use an optical lens instead of the optical fiber bundle 16 and form an optical image on the fluorescence plate 15 on the light receiving surface of the optical image detection device (CCD) 17 by the optical lens. On both sides of the fluorescence plate 15, an electrode 300 and a transparent electrode 301 are mounted and the transparent electrode 301 side applies a positive high voltage between both electrodes so as to prevent the electron beam from scattering. The optical image detection device (CCD) 17 converts and outputs the optical image formed on the light receiving surface to an electrical image signal. The outputted image signal is sent to the image processor 104 and the image signal process is performed there.

The image processor 104 comprises image signal storage units 18 and 19, an operation unit 20, and a defect detecting unit 21. The fetched image signal is displayed as an image by a monitor 22. An operation instruction and operation conditions of each unit of the apparatus are inputted and outputted from a control computer 29 in the controller 105. To the control computer 29, conditions such as an acceleration voltage when an electron beam is generated, electron beam deflection width, deflection speed, sample stage moving speed, and image signal fetching timing from the image detection device are inputted beforehand. Upon receipt of an instruction from the control computer 29, a beam controlling system 28 generates a correction signal on the basis of signals from the stage position measuring apparatus 27 and the sample height measuring apparatus 26 and sends a correction signal to an object lens power source 25 and a scanning signal generator 24 so that an electron beam is always irradiated to the correct position.

By indicating the operation conditions of the inspecting apparatus, how much the test is speeded up compared with a conventional pattern inspecting apparatus using an electron beam will be described hereunder. To test a pattern defect by the image comparison inspecting method, the image S/N ratio is required to be 10 or more. Symbol S of the S/N ratio is defined as a mean signal amount of electrons and N is defined as a 3ω value of a signal. The ω value is decided by the shot noise of the number of irradiated electrons and equal to the square root ($\sqrt{S}$) of the number of electrons S irradiated per pixel. Therefore, the S/N ratio becomes $S/(3\sqrt{S})=\sqrt{S}/3$. Furthermore, in consideration of emission of electrons from the sample, the S/N ratio becomes $\sqrt{S}/(3\sqrt{2})$. For example, to obtain an S/N ratio of about 18, $S \geq 6250$ and it is necessary to irradiate 6250 electrons per pixel. On the other hand, the resolution necessary for defect test is 0.1 μm or less. Therefore, in the conventional method for limiting an electron beam to a spot shape and scanning it on the surface of a sample, it is necessary to limit the electron beam to 0.1 μm or less. To generate such a fine beam, the beam current is limited due to the brightness of the electron source and the space charge effect and only about 100 nA at maximum can be obtained as a beam current. When the irradiated beam current is 100 nA, $100 (nA)/(1.6\times10-19 (C))=6.25\times10+11$ electrons are irradiated per second. Therefore, to irradiate 6250 electrons per pixel, an irradiation time of 10 ns is necessary. To test an area of 1 $cm^2$, a inspecting time of (1 cm/0.1 μm) $2\times10$ ns=100 s is necessary.

On the other hand, in the case of the inspection apparatus of this embodiment, an electron beam (area beam) having a beam current I is irradiated in a square region with a side of x (hereinafter, this is called 1 shot). It is assumed that by doing it, backscattering electrons η times of the irradiation current are emitted. A case that an enlarged image of the sample surface is formed by the backscattering electrons and it is detected by the image detection device (CCD) as an image of a resolution of 0.1 μm will be considered. As a comparison condition, the necessary number of signals (the number of backscattering electrons) from a square of 0.1 μm is assumed as 6250 which is the same as that of the conventional example. Assuming the required time of 1 shot as t and the time required to test an area of 1 cm² as T, t is expressed by the following formula.

$$6250 = [I \cdot \eta \cdot t/(1.6 \times 10^{-19})] \cdot [1 \times 10^{-7}/x]^2 \therefore t = 0.1 \cdot [x2/(I \cdot \eta)] \quad (1)$$

T is expressed by the following formula.

$$T = (0.01/x)^2 \cdot t \therefore T = 1 \times 10^{-4} \cdot (t/x2) = 1 \times 10^5 \cdot [1/(I \cdot \eta)] \quad (2)$$

An actual value is substituted in this formula and the test required time T is obtained.

In this embodiment, an area beam of 100 μA is irradiated into an area region of 100 μm×100 μm for 1 shot. An image detection device (CCD) having 1024×1024 pixels is used and the magnifications of the electron optical system and the imaging optical system to the CCD device are set so that 1 pixel on the CCD device corresponds to a 0.1 μm square on a sample. In this case, a distortion is generated in the periphery of an image. If an optical lens is used instead of the optical fiber bundle 16 so as to correct this distortion, an aspherical lens is used. Furthermore, a distortion which cannot be fully corrected by it is corrected by image processing before use. In this case, assuming the η value in the aforementioned formula as 0.2, the required time t for 1 shot is 50 μs and the test required time T per an area of 1 cm² is calculated as 0.5 s. The test required time requested from the shot noise of the number of irradiation electrons is greatly shortened like this and it is found that a rapid test can be realized.

Next, the setting time of the sample moving stage 8 will be described. Assuming the stage 8 moving method, for example, as a step and repeat system, the stage 8 setting time is required to be a time of the order of ms and hence the inspecting time cannot be fully shortened. Therefore, the stage 8 moving method is of a continuous moving system that the stage always moves at uniform velocity. By doing this, the restriction on the inspecting time due to the stage setting time is eliminated. However, when the stage 8 is continuously moving, the stage 8 moves even for the time of 1 shot, for example, for a period of 50 μs and the irradiation position on the sample surface is changed. Therefore, to prevent the irradiation position from changing for a period of 1 shot, the irradiation electron beam is made follow the movement of the stage 8 by the deflector 5. Viewed from the electron optical system which is a still coordinate system, the electron beam irradiation position moves, so that the image 12 formed by the imaging lens 11 also moves. To prevent this movement, the deflector 10 is made operate in link motion with the deflector 5.

Figure 3:
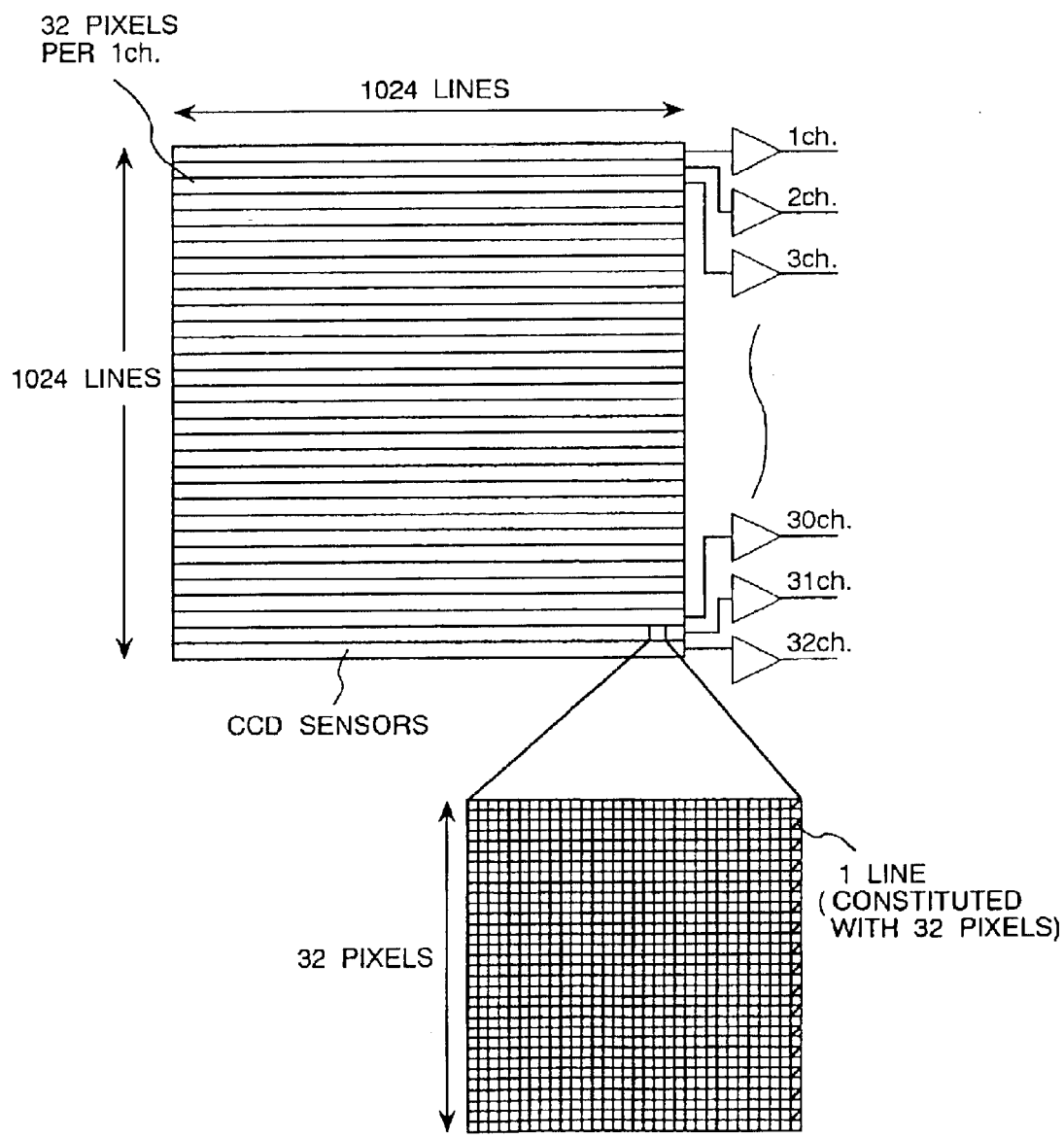
FIG. 3 is an illustration for the operation of a CCD sensor which is a component of the inspecting apparatus of the first embodiment of the present invention.

Next, the reading time of the image detection device (CCD) will be described. In this embodiment, electric charges accumulated in the CCD 17 can be read by many channels in parallel from the reading ports of 32 channels at a reading speed of 1M line/second. The number of pixels per line is 32 and the reading required time per line is 1 μs. Therefore, the reading required time per pixel is 1 (us)/32 (pixels)=32 ns. On the other hand, when a 1-channel system is used for reading image data from the CCD, reading at a very high speed such that the reading required time per pixel is 1 ns is required and it cannot be realized by the current art. In this embodiment, since a system that the reading ports of image data from the CCD are divided into 32 channels and image data is read by the 32 channels concurrently in parallel is used, the reading required time per pixel is set at 32 ns and a reading speed which can be sufficiently realized is obtained. FIG. 3 shows it schematically. The number of channels for reading image data from the CCD 17 is 32 and each channel has 32 pixels×1024 lines, so that the time required to read data of one image from the CCD is about 1 ms. Namely, an image signal in a 1 shot region of a square of 100 μm can be fetched in 1 ms and the test required time per a surface area of 1 cm² of a sample is 10 seconds. As mentioned above, compared with the test required time 100 seconds per a sample area of 1 cm² by the conventional system, speeding-up of 10 times can be realized. In this embodiment, the test required time is decided by the signal reading speed from the CCD device. Therefore, if a higher-speed data reading system is realized in the CCD device in the future, more speeding-up of the test can be expected.

Figure 2A:
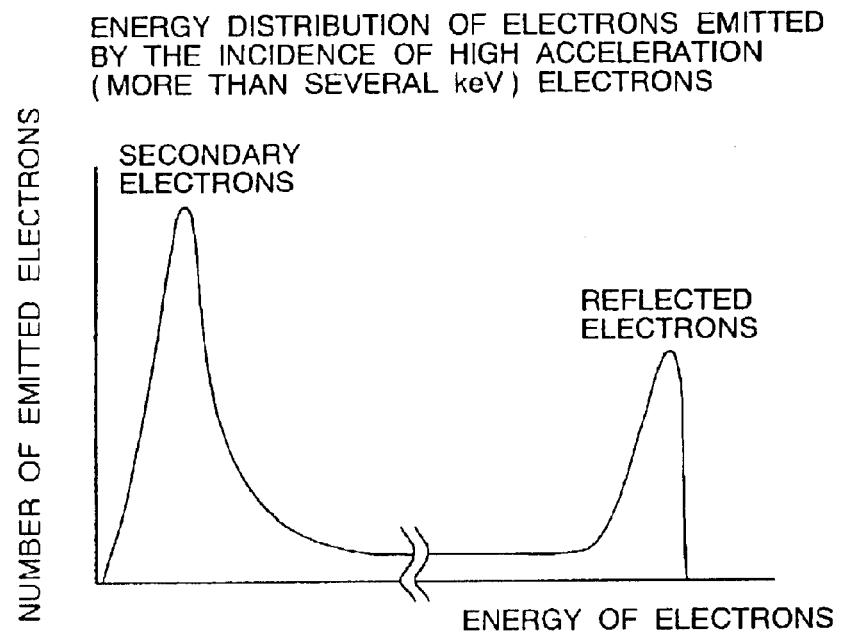
FIGS. 2(a) and 2(b) are energy distribution diagrams of emitted electrons for explaining the effects of the present invention.
Figure 2B:
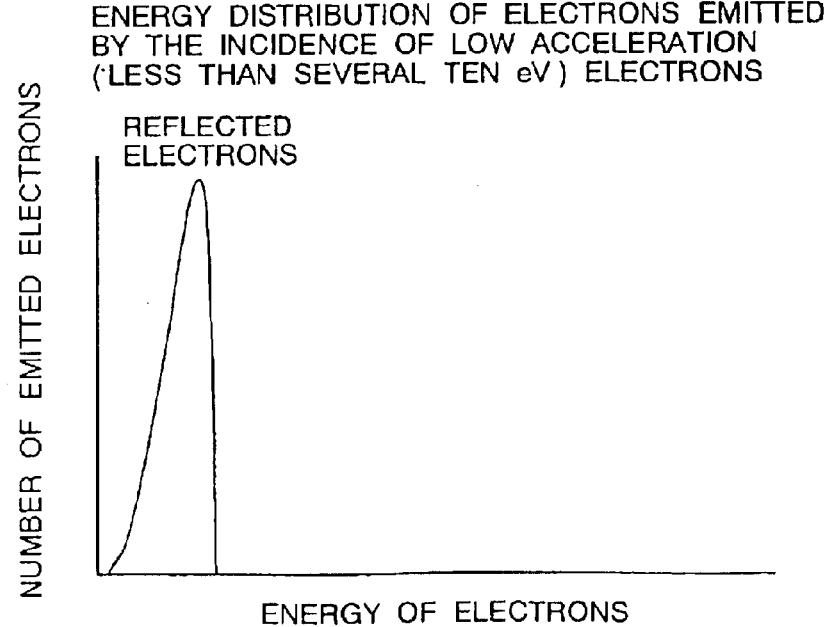

The improvement effect of inspecting speed is explained above. The other characteristics will also be described hereunder. In this embodiment, a negative high voltage is applied to the semiconductor sample 7 and the irradiation electron beam is suddenly decelerated immediately before the sample surface and irradiated. By doing this, the characteristics shown below can be obtained. Namely, when the electron beam is irradiated onto a solid sample, secondary electrons and reflected electrons are generated. Incoming electrons give energy to electrons in the solid and the electrons given the energy in the solid are emitted into the vacuum as secondary electrons. Therefore, the energy held by secondary electrons spread greatly. On the other hand, incoming electrons change the orbit by the interaction with atomic nuclei and electrons in the solid and are emitted into the vacuum once again as reflected electrons. When the interaction is only elastic scattering in this case, reflected electrons having the same energy as the incoming energy are emitted. FIG. 2 shows it schematically. When the energy of incoming electrons is high, the number of electrons entering deep inside the solid increases, so that the number of reflected electrons emitted into the vacuum once again reduces. Furthermore, since inelastic scattering increases, a wide plain is formed on the low energy side and the spread of energy increases ((a) of the drawing). When electrons having a wide spread of energy are imaged by the electron optical system, a problem arises that the resolution reduces due to the chromatic aberration. On the other hand, when electrons with low energy are irradiated, the rate of elastic scattering increases. Therefore, the plain on the low energy side reduces and emission of secondary electrons also reduces, so that the status shown in (b) of the drawing appears. Namely, in this embodiment, when electrons of low energy enter the sample surface, emission of secondary electrons having a wide spread of energy is suppressed first and the emission rate of reflected electrons, that is, backscattering electrons increases. Furthermore, since the energy spread of backscattering electrons can be minimized, there is a characteristic that an image of high resolution can be formed.

Next, the procedure for an actual inspection will be explained. Firstly, the alignment method using the optical microscope 30 and an electron beam image will be explained. The sample 7 is loaded on the sample moving stage (X-Y-θ stage) 8 and moved under the optical microscope 30. An image of the optical microscope on the surface of the sample 7 is observed by the monitor 22 and an optional pattern appearing, for example, at the center of the screen is stored. In this case, the pattern to be selected is to be a pattern which can be observed even on the electron beam image.

Next, the circuit pattern on the surface of the sample (semiconductor wafer) 7 is rotated and corrected by the X-Y-θ stage 8 so that it is set in parallel with or perpendicularly to the stage moving direction using the aforementioned image of the optical microscope. During rotation and correction, an optical image of an optional pattern portion in an optional chip of the circuit pattern on the surface of the wafer 7 at a stage position is fetched and displayed on the monitor 22 and a marking is put at an optional location on the displayed screen. And, the optical image signal is stored in the storage unit 18. Next, the stage 8 is moved in the x or y direction by the distance of several chips of the circuit pattern on the surface of the wafer 7 and an optical image of the same pattern portion as that in a new chip is fetched and displayed on the monitor 22. A marking is also put at the location corresponding to the previous marking location and the new optical image signal is stored in the storage unit 19. Next, the operation unit 20 compares and operates the optical image signals stored in the storage units 18 and 19 and calculates the shift, amount of the marking location between both images. From the shift amount of the marking location and the stage moving distance between both images, the operation unit 20 calculates the rotation angle error of the wafer 7, rotates the stage 8 by the error, and corrects the rotation angle. The aforementioned rotation correction operation is repeated several times until the rotation angle error is reduced below the predetermined value. Furthermore, the circuit pattern on the surface of the wafer 7 is observed using the image of the optical microscope, and the chip position on the wafer and the distance between chips (for example, the repetitive pitch of the repetitive pattern such as the memory cell) are measured beforehand, and the values are inputted to the control computer 29. The chip to be tested on the surface of the wafer 7 and the region to be tested in the chip are set on the image of the optical microscope of the monitor 22. The optical microscope image can be observed at a comparatively lower magnification and even if the circuit pattern on the surface of the wafer 7 is covered with a transparent film such as a silicon dioxide film, the base thereof also can be observed. Therefore, the layout of the intra-chip circuit pattern can be simple observed and the inspection region can be set simply.

Next, the sample (wafer) 7 is moved under the electron optical system. Then, an electron beam is irradiated onto the region which is expected to include the inspection region previously set on the optical microscope image and an electron beam image is obtained. In this case, the aforementioned inspection region is set so as to be included-in the electron beam irradiation region of 1 shot. The stage 8 is moved so that the pattern in the previously marked location appears on the same screen as that used to mark on the previous optical microscope image even on this electron beam image. By doing this, the electron beam irradiation position and the optical microscope observation position can be associated with each other before start of the test and the electron beam irradiation position can be calibrated. On this electron beam image, the same operation as that previously performed on the optical microscope image is executed. By doing this, simple checking of the observation position and positioning and adjustment of the electron beam irradiation position can be realized. Furthermore, by using an electron beam image which has a higher resolution compared with an optical microscope image and can obtain a high-powered image after a certain degree of rotation correction is executed, more highly accurate rotation correction can be performed. In addition, by use of this electron beam image, the inspection region or the same pattern region can be observed, checked, and corrected at a high magnification and with high precision. However, when the whole (or a part) of the surface of the semiconductor wafer 7 is covered with an insulator, if an electron beam is irradiated, the insulator is charged and the location where the electron beam is irradiated once may not be inspected. Therefore, to irradiate an electron beam for setting of inspection conditions prior to the aforementioned inspection, it is desirable to select a location which is a region not scheduled to be actually inspected and has the same pattern as that of the inspection region.

When the aforementioned setting of inspection conditions is completed, an electron beam image of a part of the inspection region on the surface of the semiconductor wafer 7 is formed under the same conditions as the actual inspection conditions and information of the image brightness depending on the material and shape of the inspection region and its variation range are calculated, given in a table, and stored. The stored table is referred to in the later inspection process and decision conditions for deciding whether the pattern portion in the inspection region which is actually imaged and detected is defective or not are determined.

When the setting of the inspection region and defect detecting conditions is completed by the aforementioned procedure, the test is actually started. During the test, the stage 8 with the sample (semiconductor wafer) 7 loaded continuously moves in the X direction at a constant speed. During the period, the electron beam is irradiated into the same irradiation region (area region) on the surface of the wafer 7 for a fixed shot time (50 μs or more in this embodiment) for each 1 shot. Since the stage 8 continuously moves, the electron beam is deflected and scanned by the deflector 5 by following the movement of the stage 8.

The irradiation region or irradiation position of the electron beam is always monitored by the stage position measuring apparatus 27 and the sample height measuring apparatus 26 installed on the stage 8. These monitor informations are transferred to the control computer 29, and the position shift amount is grasped in detail, and this position shift amount is accurately corrected by the beam controlling system 28. By doing this, accurate positioning necessary for the pattern comparison test is executed at high speed and with high precision.

The surface height of the semiconductor wafer 7 is measured in real time by a means other than an electron beam and the focal lengths of the object lens 6 and the imaging lens 11 for irradiating an electron beam are dynamically corrected. As a means other than an electron beam, for example, the optical height measuring apparatus 26 by a laser interference system or a system for measuring a position change of reflected light is used. By doing this, an electron beam image focusing on the surface of the inspection region can be always formed. By measuring the warp of the wafer 7 before starting the test and executing the aforementioned focal length correction on the basis of the measured data, measurement of the surface height of the wafer 7 may be made unnecessary during the actual test.

The electron beam is irradiated onto the surface of the semiconductor wafer 7 and an enlarged optical image of the desired inspection region (area region) on the surface of the wafer 7 is formed on the fluorescence plate 15 by reflected electrons (backscattering electrons). The enlarged optical image is converted to an electrical image signal by the CCD device 17 and the image signal is fetched by the image processor 104. Upon receipt of an instruction from the control computer 29, the image signal is stored in the storage unit 18 (or 19) as an electron beam image signal of the area region corresponding to the electron beam irradiation position given by the controller 28.

When the pattern comparison test is to be executed between the adjacent chips A and B having the same design pattern formed on the surface of the semiconductor wafer 7, an electron beam image signal of the inspection region in the chip A is fetched first and stored in the storage unit 18. Next, an image signal of the inspection region in the adjacent chip B corresponding to the aforementioned inspection region is fetched and stored in the storage unit 19 and compared with the stored image signal in the storage unit 18 at the same time. Furthermore, an image signal of the corresponding inspection region in the next chip C is fetched and it is overwritten and stored in the storage unit 18 and compared with the stored image signal of the inspection region in the chip B in the storage unit 19 at the same time. Such an operation is repeated and image signals of the inspection regions corresponding to each other in all the testing chips are sequentially stored and compared.

In addition to the aforementioned method, a method for storing an electron beam image signal of the desired inspection region of a standard acceptable (non-defective) sample in the storage unit 18 beforehand may be used. In this case, the inspecting region and inspection conditions of the aforementioned acceptable sample are inputted to the control computer 29 beforehand, and the test is executed with the aforementioned acceptable sample on the basis of these inputted data, and the obtained image signal of the desired inspection region is stored in the storage unit 18. Next, the sample 7 to be inspected is loaded on the stage 8 and the test is executed according to the same procedure as the previous one. The obtained image signal of the inspection region corresponding to the aforementioned one is fetched into the storage unit 19 and the image signal of this sample to be inspected and the image signal of the acceptable sample stored in the storage unit 18 beforehand are compared at the same time. By doing this, the existence of a pattern defect of the aforementioned desired inspection region of the sample to be inspected is detected. As the aforementioned standard (acceptable) sample, a sample (wafer) which is found beforehand not to have a pattern defect may be used separately from the sample to be inspected or the region (chip) on the surface of the sample to be inspected which is found beforehand not to have a pattern defect may be used. For example, when a pattern is to be formed on the surface of a semiconductor sample (wafer), an alignment shift defect may be generated between the lower layer pattern and the upper layer pattern overall the wafer. If this occurs, when the comparison objects are patterns in the same wafer or the same chip, the aforementioned defect (failure) generated overall the wafer may be overlooked. However, according to this embodiment, an image signal of the region which is found beforehand to be acceptable (non-defective) is stored and this stored image signal and the image signal of the region to be tested are compared, so that the aforementioned defect generated overall the wafer can be detected precisely.

Both image signals stored in the storage units 18 and 19 are fetched into the operation unit 20 respectively and various statistics (concretely, a mean value of image densities, statistics of dispersion and others) and differential values between peripheral pixels are calculated on the basis of the already obtained defect detecting conditions. Both image signals subjected to these processes are transferred into the defect detecting unit 21 and compared by it and a difference signal between both image signals is extracted. This difference signal and the already obtained and stored defect detecting conditions are compared and a defect is decided. The image signal of the pattern region which is decided as defective and image signals in the other regions are discriminated.

By forming an image by reflected electrons (backscattering electrons or secondary electrons) generated from the semiconductor sample 7 and comparing and testing an image signal of the corresponding pattern region by the inspecting method and inspection apparatus described above, the existence of a pattern defect can be detected. By doing this, compared with a conventional inspection apparatus using an electron beam, a very rapid test can be realized.

Embodiment 2

In the aforementioned Embodiment 1, the area of the electron beam irradiation region of 1 shot is considerably large such as 100 $\mu$m×100 $\mu$m, so that a problem may arise that a distortion is generated in the periphery of the enlarged image of the semiconductor sample or that the beam current density in the irradiation region becomes ununiform. When an image distortion or ununiformity of current density is fixedly generated, it can be corrected by changing the fiber strand layout of the optical fiber bundle 16. The obtaining sensitivity of an image signal and weighting of the image process can be corrected. However, if they vary in time, it is hard to handle by those methods. In this embodiment, the irradiation region of 1 shot is a square of 5 $\mu$m and it is designed to prevent the problems of distortion and ununiformity of current density. The irradiation electron beam current is 5 $\mu$A per 1 shot. In this case, assuming the electron scattering efficiency $\eta$ as 0.2, from the formula (1) shown previously, the electron beam irradiation time t per 1 shot is 2.5 $\mu$s. After the electron beam is irradiated into an irradiation region (5 $\mu$m square) for a shot time of 2.5 $\mu$s, the electron beam is moved into the next adjacent irradiation region (5 $\mu$m square) by the deflector 5. The electron beam moves to the irradiation position one by one in this way and irradiates the whole range of 100 $\mu$m in the x direction×100 $\mu$m in the y direction by 20×20=400 shots.

Figure 4:
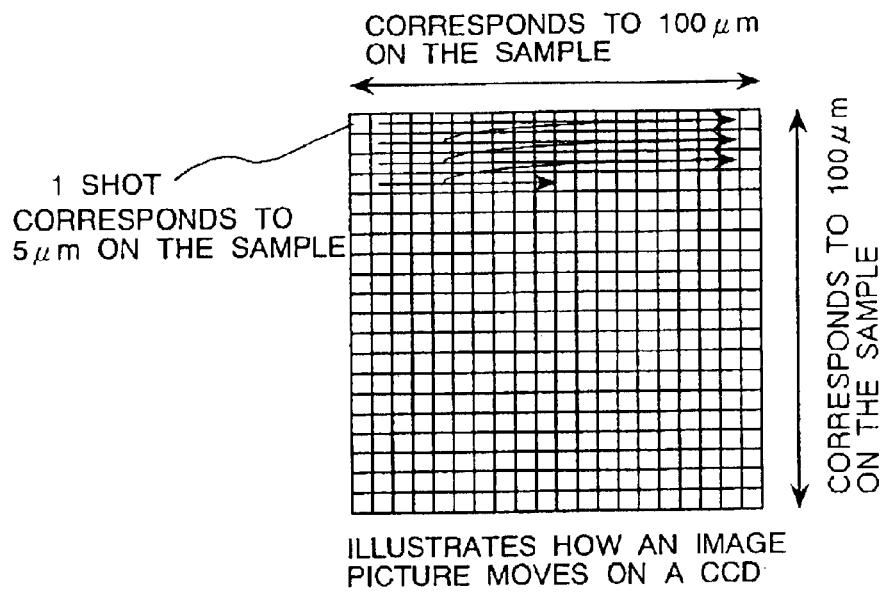
FIG. 4 is an illustration for the operation of the inspection apparatus of the second embodiment of the present invention.

In this case, an enlarged image is obtained in the position on the CCD device corresponding to the electron beam irradiation position at that time for each 1 shot and the enlarged image position obtained on the CCD device also moves according to the movement of the electron beam irradiation position due to scanning of the electron beam. FIG. 4 shows this situation. As the CCD device 17, a CCD device of 1024×1024 pixels is used. 1 pixel on the CCD device is equivalent to a region of a square of 0.1 $\mu$m on the surface of the sample 7 and hence the irradiation region (5 $\mu$m square) of 1 shot on the surface of the sample 7 is a region of 50×50 pixels (equivalent to $\frac{1}{400}$ of the whole light receiving surface of the CCD device) on the light receiving surface of the CCD device. The whole light receiving surface of the CCD device can cover a region of a square of 100 $\mu$m on the sample surface. Therefore, to obtain an enlarged image of a region of a square of 100 $\mu$m on the sample surface, 2.5 (us)×400 (shots)=1 (ms) is required.

When an image of a region of a square of 100 $\mu$m on the surface of the sample 7 is formed on the CCD for 1 ms as mentioned above, the image signal accumulated in the CCD is stored in the image storage unit 18 as a digital signal. To obtain an image signal of the next adjacent region on the sample surface, it is necessary to move the stage 8 100 μm. For this stage movement, the system that the stage 8 continuously moves at a constant speed is used in the same way as with Embodiment 1. In this case, the irradiation electron beam is deflected and scanned by the deflector 5 by following the movement of the stage 8 so that the stage 8 enters the state that as if it is at a standstill for the irradiation electron beam. By doing this, the useless time generated when the stage 8 is moved or stopped is reduced to zero. For following scanning of the irradiation electron beam to continuous movement of the stage 8, the beam controlling system 28 refers to a signal from the stage position measuring apparatus 27, calculates a deflection correction signal, sends the deflection correction signal to the deflector 5, and makes the deflector 5 control the deflection of the irradiation electron beam. Furthermore, by superimposing a distortion of an enlarged image of a sample due to the electron beam and a correction regarding a position drift on the aforementioned deflection correction signal, these corrections are also carried out. When the deflector 10 is operated in link motion with the deflector 5, the position of the enlarged image of the sample on the CCD will not be affected by the beam position movement due to the following of the stage. By doing this, the useless time due to stage movement is eliminated and a test at high speed and with high precision can be realized. The image process for the defect test after the aforementioned process is the same as that of the aforementioned Embodiment 1.

When the test proceeds according to the aforementioned procedure, the time T required to sequentially form an enlarged image per 1 cm² of the sample surface on the CCD is 10 seconds. On the other hand, an image signal is read from the CCD at a reading speed of 1M line/second in the same way as with the aforementioned Embodiment 1, so that 1 ms is required to read one image (image of a square of 100 μm of the sample surface) and hence 10 seconds are required for a surface area of 1 cm² of the sample. Since image forming on the CCD device and reading of an image signal are carried out in parallel, the time required for the test is the longer time among the time required for image forming and the time required for image signal reading. In this embodiment, the time required for image forming and the time required for image signal reading are equal to each other such as 10 seconds per a surface area of 1 cm² of the sample and hence the test required time for a surface area of 1 cm² of the sample in this embodiment is 10 seconds.

In this embodiment, compared with the aforementioned Embodiment 1, the electron beam irradiation area per 1 shot is smaller. Therefore, a small irradiation beam current is acceptable, so that as the electron source 1, compared with the LaB6 electron source whose end is spread in the aforementioned Embodiment 1, an LaB6 electron source whose end is sharper is used. In this embodiment, a heat field emission type electron source, for example, a Zr/O/W electron source may be used in place of the LaB6 electron source.

In the above explanation, an example of a case that the electron beam irradiation region of 1 shot is fixed to the size of a square of 5 μm is shown. It is possible to make the size of this electron beam irradiation region variable according to the pattern repetitive pitch on the surface of the semiconductor sample 7. As mentioned above, in this embodiment, the electron beam irradiation region of 1 shot is set smaller. Therefore, even if a slight distortion is generated in the connection of each irradiation region, a nearly similar distortion is always generated in the same location and distortions on two images to be mutually compared are generated in the same way, so that the problem of maldetection due to distortion is eliminated. By doing this, a highly reliable patterned wafer inspection can be realized.

Embodiment 3

In this embodiment, as a device for converting a sample surface image to an electric signal, a time accumulative CCD sensor is used. This sensor is called a TDI sensor and generally used in an optical inspecting apparatus. The constitution other than it is the same as that of the aforementioned Embodiment 2. The operation concept of the TDI sensor will be explained by referring to FIG. 5. The TDI sensor operates so as to move the charge generated according to the intensity of the light received by each light receiving region to the line in the x direction and sequentially add the charge generated according to the intensity of the light received by the moving destination at the same time. Upon arrival at the last line of the light receiving surface, the TDI sensor outputs it to the outside as an electric signal. Therefore, when the moving speed of the charge in the x direction is made equal to the moving speed of an image on the light receiving surface in the x direction, a signal during moving of the image on the sensor is integrated and outputted.

Figure 5:
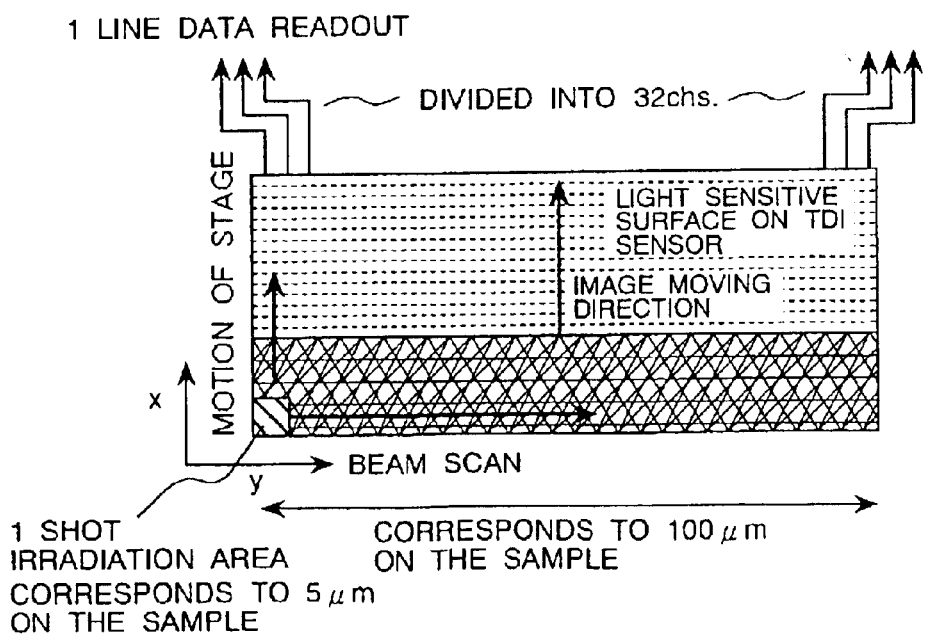
FIG. 5 is an illustration for the operation of a TDI sensor which is a component of the inspection apparatus of the third embodiment of the present invention.

In this embodiment, in the same way as with the CCD sensor in the aforementioned Embodiments 1 and 2, signal reading is divided into 32 channels and the channels read signals in parallel with each other and hence a reading speed of 1M line/second is realized. The size of the light receiving region is 64 pixels in the x direction and 1024 pixels in the y direction. The length of one line in the x direction is equivalent to 0.1 μm on the sample surface and the length in the y direction is equivalent to about 100 μM. In this case, an image 0.1 μm in length and 100 μm in width is outputted at a speed of 1 M/s, so that the continuous moving speed of the stage is set at the same speed (0.1 μm/1 μs=100 mm/s). As mentioned above, the movement of the inspection region in the x direction is carried out by moving the stage 8. On the other hand, since the irradiation region of 1 shot is a square of 5 μm, as shown in FIG. 5, it is necessary to scan the electron beam so as to move the irradiation region in the y direction. Namely, it is necessary to scan the electron beam 100 μm in the y direction while the stage 8 moves in the x direction for 1 shot (5 μm). Assuming the required time for 1 shot as 2.5 μs, it requires 50 μs to scan 100 μm (for 20 shots) in the y direction. On the other hand, since the moving speed of the stage 8 in the x direction is 100 mm/s, the time required for movement of just 1 shot (5 μm) of the stage 8 in the x direction is 50 μs. By matching the time required for movement of 1 shot (5 μm) of the stage in the x direction with the time required for scanning of 20 shots (100 μm) of the electron beam in the y direction like this, an occurrence of useless time is prevented. To obtain an image of a surface area of 1 cm² of the sample by this method, a time of 2×10⁵ times of the scan required time (50 us) for the aforementioned unit scanning region of 5 μm×100 μm, so that the test required time per a surface area of 1 cm² of the sample is 10 seconds. If the signal output speed from the TDI sensor can reach 2M line/s which is 2 times of the aforementioned example, the test required time will be halved such as 5 seconds.

As mentioned above, in this embodiment, the stage moving speed depending on the signal output speed of the TDI sensor is 100 mm/s, so that the movement of the inspection region in the x direction due to stage movement is sufficiently available. Moreover, a sufficient time can be reserved for scanning of the electron beam in the y direction in the inspection region during the period. Furthermore, in this embodiment, the signal output speed of the TDI sensor decides the inspecting speed. Therefore, if the signal output speed is improved, a more rapid test can be realized.

Embodiment 4

In the aforementioned Embodiments 1 to 3, a decelerated electron beam is irradiated onto the surface of a semiconductor sample. However, in this embodiment, so as to allow an electron beam to reflect immediately before the surface of a sample without entering the sample surface, a negative potential slightly higher than the acceleration voltage of the electron beam is applied to the sample surface. To form a surface image of the sample, the electron beam reflected immediately before the sample is used. The constitution other than it is exactly the same as that of the aforementioned Embodiment 1. Recently, the surface grinding process such as CMP or CML has been introduced into the semiconductor process and there is a trend that the uneven surface of a semiconductor sample is flattened. In this embodiment, fine irregularities of the surface after such a flattening process can be detected with high sensitivity compared with the aforementioned Embodiment 1. Namely, the characteristic of this embodiment is that the negative voltage to be applied to a sample can be made higher compared with the aforementioned Embodiments 1, 2, and 3. Therefore, a condition that an irradiation electron beam does not actually enter a semiconductor sample, interacts with atomic nuclei and electrons existing on the sample surface, and is reflected immediately before the sample surface is set. When the test is executed under such a condition, an advantage can be obtained that a defect of the process which appears as a change of fine irregularities of the surface can be detected with higher sensitivity than the case of Embodiment 1.

Embodiment 5

Figure 6:
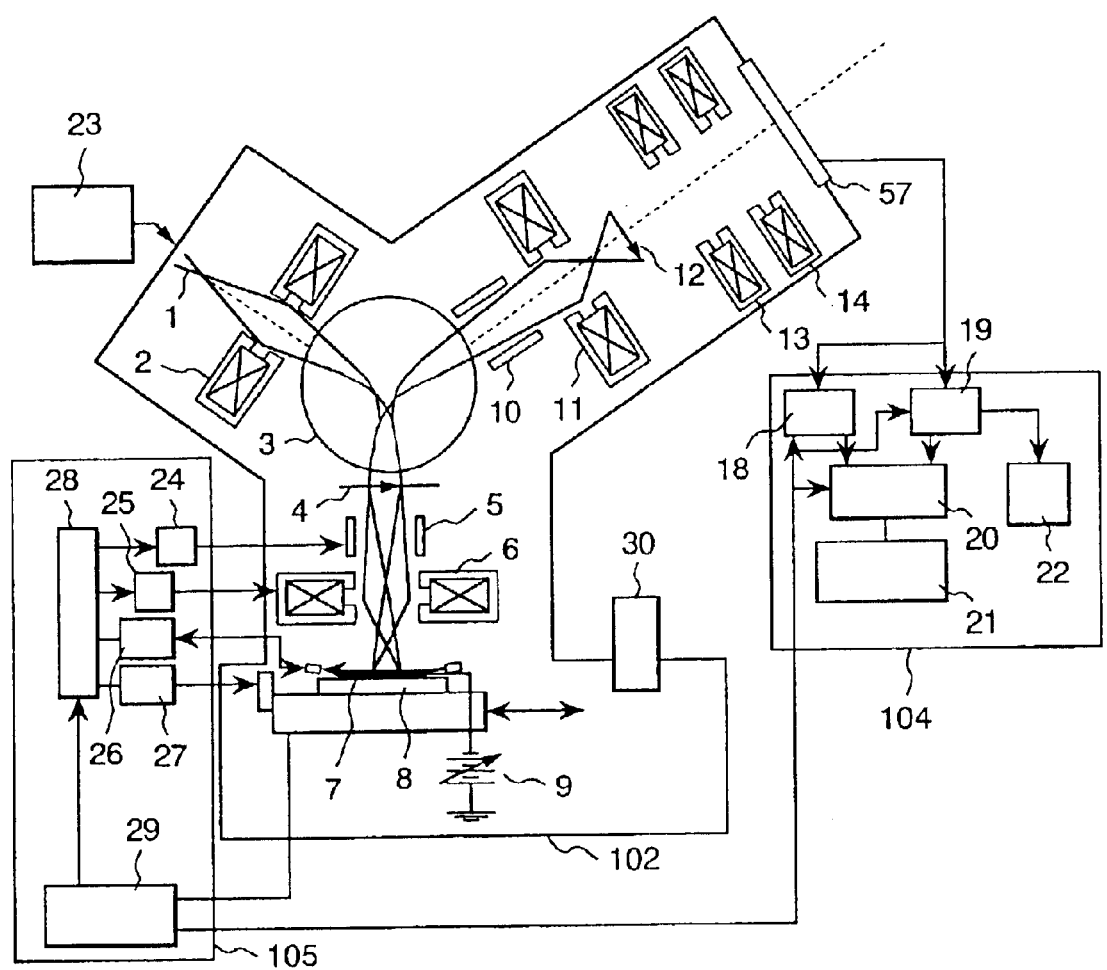
FIG. 6 is a schematic view of the inspection apparatus of the fifth embodiment of the present invention.

In the aforementioned Embodiments 1 to 4, an electron beam image is converted to an optical image using a fluorescence plate and then the image is detected by an optical sensor (CCD or TDI). In this embodiment, a sensor 57 which is directly sensitive to an electron beam is used and hence the fluorescence plate and optical fiber bundle in the aforementioned Embodiments 1 to 4 are omitted. FIG. 6 shows its schematic view. The sectional structure of the sensor 57 is that a conductive film of several hundreds angstroms is coated on the outer surface of the light receiving surface of a normal optical sensor. By doing this, an image of the sample surface by the electron beam can be directly detected, so that an optical fiber bundle (or an optical lens in place of it) and a fluorescence plate as indicated in the aforementioned Embodiments 1 to 4 are not necessary and the apparatus constitution is simplified. As a result, error factors are reduced and a more highly reliable test can be executed.

Embodiment 6

Figure 7:
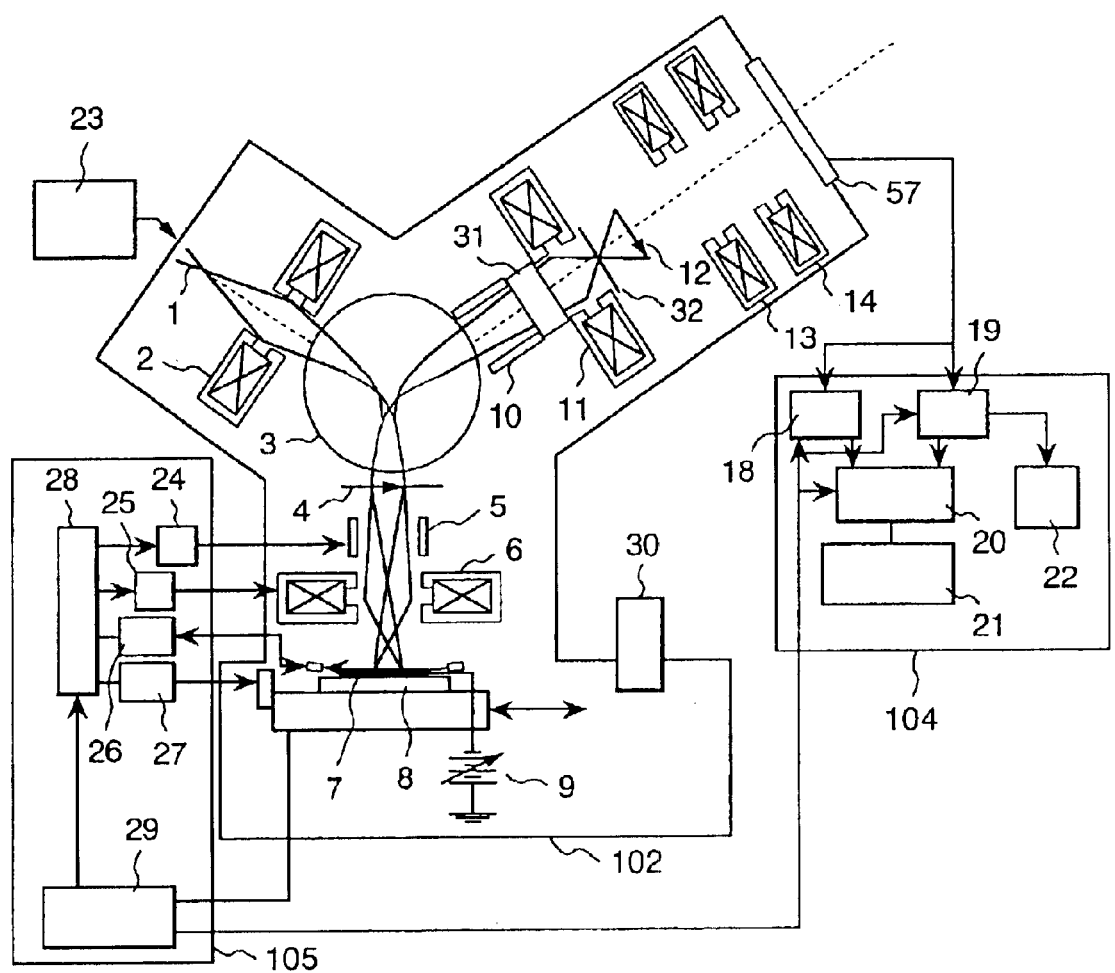
FIG. 7 is a schematic view of the inspection apparatus of the sixth embodiment of the present invention.
Figure 8:
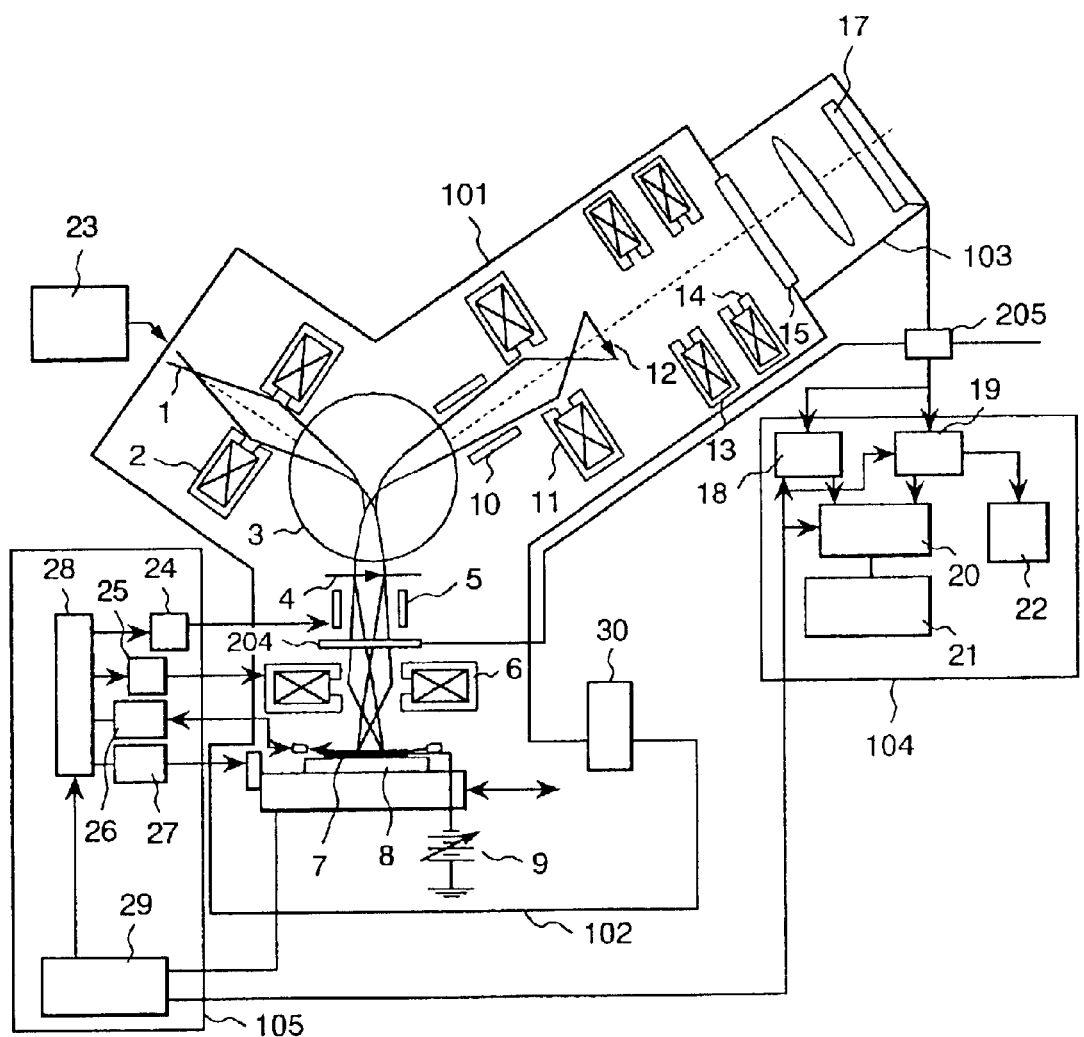
FIG. 8 is a schematic view of the inspection apparatus of the seventh embodiment of the present invention.

In the aforementioned Embodiments 1 to 3 and 5, a negative potential is applied to the semiconductor sample 7 and the energy of electrons irradiated onto the sample is made smaller, so that an effect that the energy dispersion of backscattering electrons emitted from the sample is made smaller can be obtained. In this embodiment, an energy filter 31 is newly installed between the semiconductor sample 7 and the imaging lens 11 and the energy dispersion of electrons forming a testing image is made more smaller. FIG. 7 shows an example of the apparatus constitution. As the energy filter 31, a filter called a Wien filter combining electrostatic deflection and electromagnetic deflection is used. The Wien filter functions to allow an electron beam having some specific energy to go straight on without deflection by offsetting the electrostatic deflection action and the electromagnetic deflection action each other. Therefore, when an aperture 32 is installed behind the imaging lens 11 at the later stage of the energy filter 31, it is possible that only the electron beam having specific energy passes through the opening of the aperture 32 and forms an electron beam image of the sample. Therefore, there is an effect that the chromatic aberration by the imaging lens 11 and the magnifying lenses 13 and 14 is reduced and the resolution of an image formed on the sensor 57 (or the fluorescence plate 15) is improved.

Embodiment 7

In this embodiment, an aperture-sensor 204 which has the same function as that of the sensor 57 used in the previous Embodiment 5 (FIG. 6) and Embodiment 6 (FIG. 7) and is equipped with a beam passing hole at its center is installed in just the location where a reverse space image (Fourier transformation image) of the electron beam irradiation region on the semiconductor sample 7 is formed. An electron beam intensity distribution image (signal) from the aperture-sensor 204 is inputted to the image storage units 18 and 19 in the image processor 104 via a signal switching apparatus 205. Namely, upon receipt of a control signal from the control computer 29, the signal switching apparatus 205 functions so as to select one of an image signal from the aperture-sensor 204 and an image signal from the CCD 17 and supply it to the image storage units 18 and 19 in the image processor 104.

The reverse space image (Fourier transformation image) of the electron beam irradiation region on the surface of the semiconductor sample 7 is formed on the surface where backscattering electrons emitted from the sample surface at the same scattering angle are imaged at one point by the object lens 6. Since a circuit pattern formed on the surface of a semiconductor sample is generally based on the well-regulated repetitive structure, its reverse space image is a simple image comprising a small number of spots and lines. Therefore, comparison between reverse space images of different regions is easier than comparison between respective corresponding real space images. Therefore, by use of this reverse space image comparison, decision of existence of a defect in the electron beam irradiation region can be executed more effectively and with higher reliability compared with a case using real space image comparison. However, needless to say, form the aforementioned reverse space image comparison, the location in the electron beam irradiation region where a defect exists can be identified. Therefore, in this embodiment, firstly by the comparison inspection using a reverse space image signal from the aperture-sensor 204, the existence of a defect in the region to be tested is decided simply and quickly. Next, by the comparison test using a real space image signal from the CCD sensor 17, the existing position of the defect can be accurately identified. By doing this, the outline of the defect occurrence region can be simply known prior to the detailed defect position identification by the real space image comparison and a highly efficient defect inspection can be realized.

Needless to say, the installation position of the aperture-sensor 204 is not always limited only to the later stage position of the object lens like this embodiment if it is a position where a reverse space image of the electron beam irradiation region is formed. Furthermore, needless to say, if the aforementioned Embodiments 1 to 6 are also subjected to the same constitution change as that of this embodiment, the same effect as that of this embodiment can be realized.

According to the present invention, the inspection speed of a wafer pattern inspection apparatus using an electron beam is greatly speeded up.

The invention claimed is:

1. A patterned wafer inspection apparatus comprising:

a sample stage to hold a wafer to be inspected, an electron beam source to radiate an area electron beam, an acceleration power source to give first potential to accelerate the area electron beam radiated from the electron beam source, means for irradiating the accelerated area electron beam to the wafer, means for giving second potential to a surface of a wafer to be inspected to reflect the area electron beam before the area electron beam reaches a surface of a wafer to be inspected, an image detector including a plurality of pixels to detect the reflected electron beam, an image processor to in inspect a wafer to be inspected by comparing images obtained by the image processor, wherein said area electron beam is defined so that a reflected area of the area electron beam detected by the detector corresponds to the plurality of the pixels.

2. A patterned wafer inspection apparatus, according to claim 1, wherein an absolute value of the second potential is greater than the absolute value of the first potential.

3. A patterned wafer inspection apparatus, according to claim 1, wherein said image detector is comprised of TDI sensor.

4. A patterned wafer inspection apparatus, according to claim 3, wherein:

said means for accelerating the area electron beam is comprised of a first power source to give a first potential to the area electron beam, said means for reflecting the area electron beam is comprised of second power source to give a second potential to a wafer to be inspected, and an absolute value of the first potential is less than that of the second potential.

5. A patterned wafer inspection apparatus, comprising:

a sample stage to hold a wafer to be inspected, an electron beam source to radiate an area electron beam, means for accelerating the area electron beam radiated from the electron beam source, means for irradiating the accelerated area electron beam to a wafer to be inspected, means for reflecting the area electron beam just before the area electron area beam reaches a surface of wafer to be inspected, means for detecting a reflected area electron beam including at least two pixels, means for forming an image from the reflected area electron beam detected by the detecting means, means for finding a defect in a wafer to be inspected by comparing the images, wherein said area electron beam is defined so that a reflected area of the area electron beam detected by the detector corresponds to the plurality of the pixels.

6. A sample defect inspection apparatus comprising:

a sample stage for holding a sample to be inspected, an electron optical system to radiate an electron beam to the sample held on the sample stage, a power source to apply a predetermined voltage to the sample stage, an electron detector, a processing unit, wherein the electron beam radiated to a sample to be inspected is reflected before a surface of the sample without entering the surface of the sample by the application of the predetermined voltage to the sample, the detector detects the reflected electron beam, the signal processing unit processes a signal from the detector by the detection of the electron beam, and detects a defect formed in a sample to be inspected.

7. A sample defect inspection apparatus comprising:

an electron optic system to radiate an area electron beam to a sample to be inspected, a power source to apply a predetermined voltage to a sample to be inspected, an electron detector to detect the reflected electron from a sample to be inspected, an image processor, wherein the radiated electron beam is reflected just before reaching a surface of a sample to be inspected, and said image processing unit forms an image of a sample to be inspected and analyzes the image to detect a defect in a sample to be inspected.

* * * * *